United States Patent [19]

Oh

[11] Patent Number: 4,883,490

[45] Date of Patent: Nov. 28, 1989

[54] ACETABULAR CUP

[76] Inventor: Indong Oh, 851 Lyndon St., S. Pasadena, Calif. 91030

[21] Appl. No.: 587,311

[22] Filed: Mar. 7, 1984

Related U.S. Application Data

[63] Continuation-in-part of Ser. No. 340,024, Jan. 18, 1982, Pat. No. 4,437,193.

[51] Int. Cl.[4] ............................................. A61F 2/34
[52] U.S. Cl. ................................................... 623/22
[58] Field of Search ................... 3/1.5, 1.51, 1.512, 3/1.513; 128/92 C, 92 CA

[56] References Cited

U.S. PATENT DOCUMENTS

| | | |
|---|---|---|
| D. 232,004 | 7/1974 | Amstutz . |
| D. 232,005 | 7/1974 | Farling . |
| D. 235,377 | 6/1975 | Medcraft . |
| 3,698,017 | 10/1972 | Scales et al. . |
| 3,722,002 | 3/1973 | Charnley . |
| 3,774,244 | 11/1973 | Walker ................... 623/20 |
| 3,840,904 | 10/1974 | Tronzo . |
| 4,031,570 | 6/1977 | Frey . |
| 4,123,806 | 11/1978 | Amstutz et al. ............. 3/1.512 |
| 4,262,369 | 4/1981 | Roux . |
| 4,285,071 | 8/1981 | Nelson et al. ............. 3/1.512 |
| 4,327,449 | 5/1982 | Charnley ............. 3/1.512 |
| 4,437,193 | 3/1984 | Oh ............. 3/1.512 |

FOREIGN PATENT DOCUMENTS

| | | |
|---|---|---|
| 2225812 | 1/1974 | Fed. Rep. of Germany ....... 3/1.312 |
| 2314175 | 9/1974 | Fed. Rep. of Germany ....... 3/1.512 |
| 2325585 | 11/1974 | Fed. Rep. of Germany ....... 3/1.512 |
| 1334584 | 10/1973 | United Kingdom ................... 623/22 |

OTHER PUBLICATIONS

"Bard Contour", SP-Prosthesis Cup, Link.

Primary Examiner—Richard J. Apley
Assistant Examiner—D. Isabella
Attorney, Agent, or Firm—Gordon L. Peterson

[57] ABSTRACT

An acetabular cup of approximately hemispherical configuration adapted for implantation in the acetabulum and having an outer surface with a generally part-spherical contour and an inner concave bearing surface adapted to receive a femoral head. The outer surface has a plurality of grooves defining segments, and the grooves are adapted to receive, and interlock with, cement for affixing the acetabular cup within the acetabulum. At least one of the grooves has an undercut which defines an overhanging flange. Cement is received in such groove behind the flange to interlock with the flange and to resist loosening of the acetabular cup from the acetabulum. The acetabular cup has spacer lugs on the segments, and a radiopaque marker is embedded in one of the segments in a polar region of the acetabular cup.

14 Claims, 3 Drawing Sheets

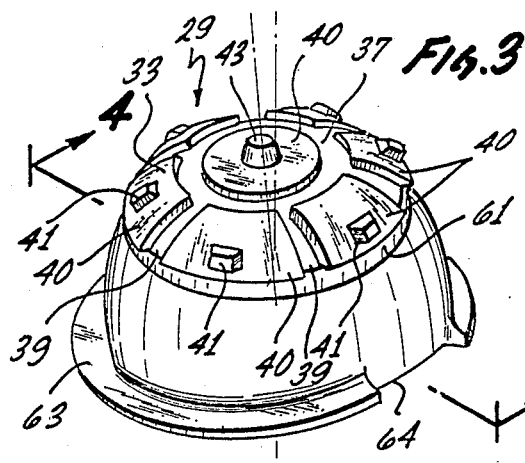
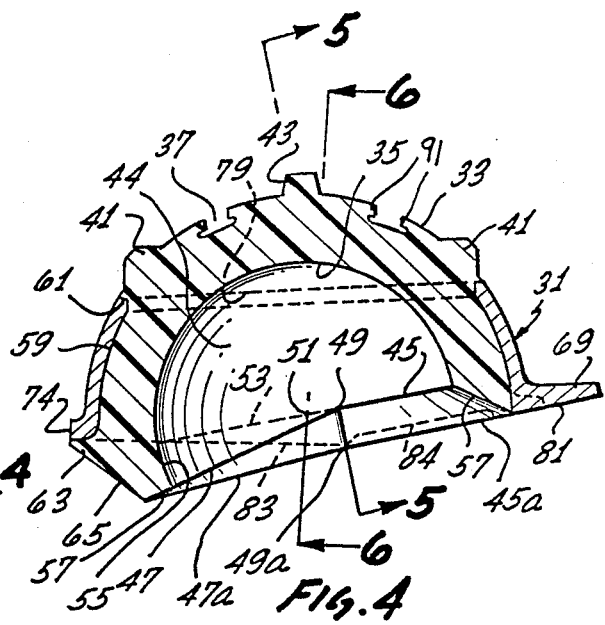
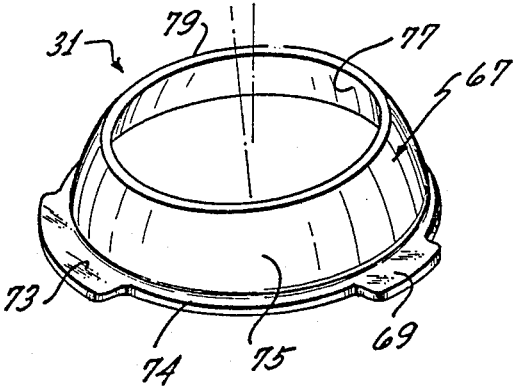
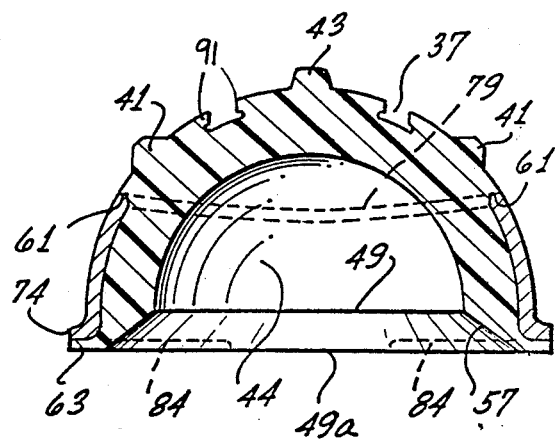
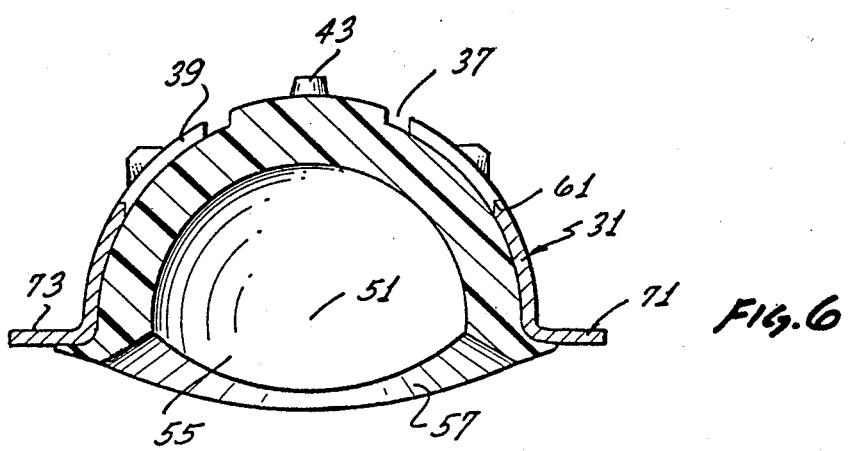

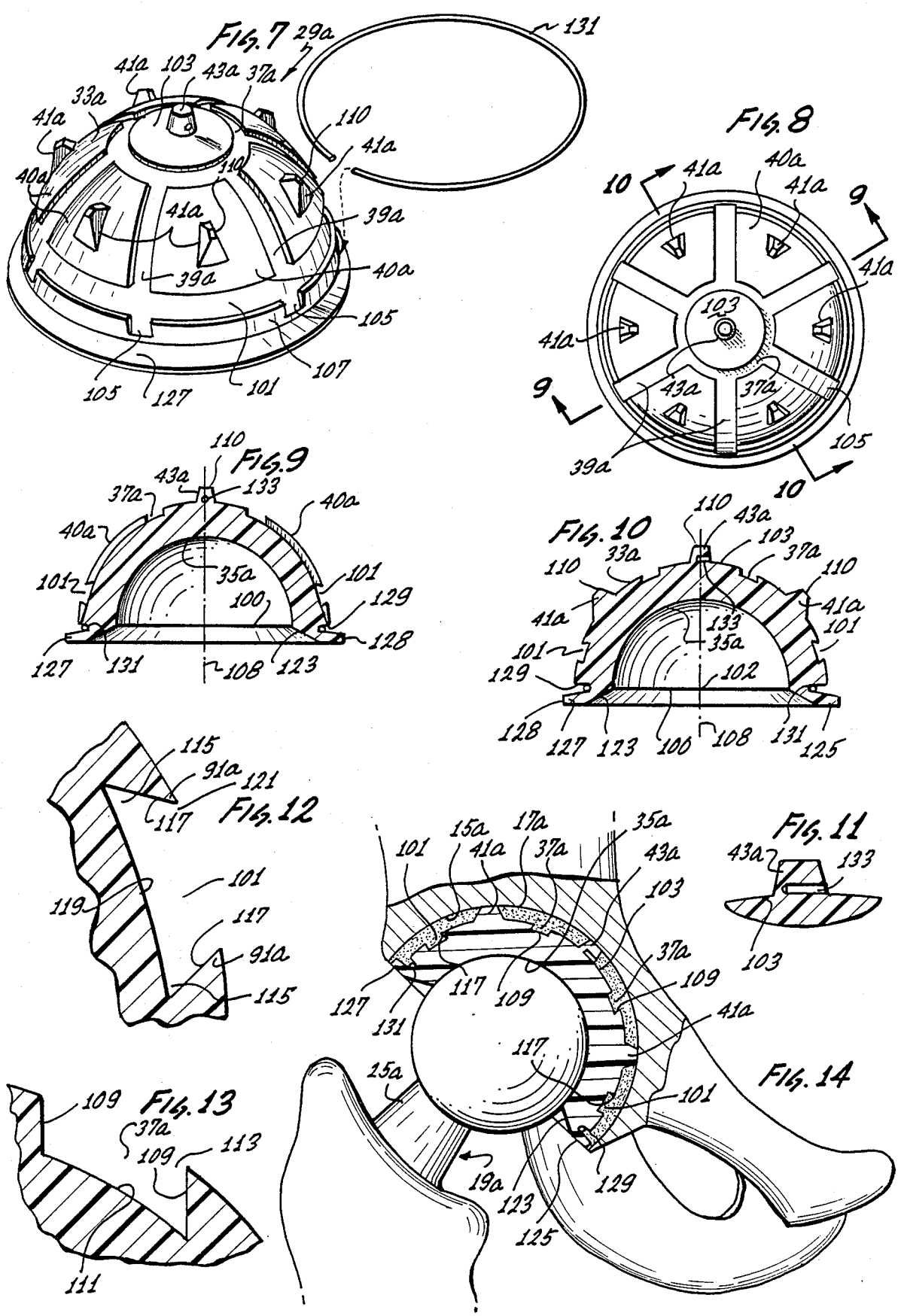

ACETABULAR CUP

BACKGROUND OF THE INVENTION

This application is a continuation in part of application Ser. No. 340,024 filed Jan. 18, 1982; and entitled Protrusio Cup.

A hip joint comprises a socket or acetabulum and a femoral head or ball received in the acetabulum. Thus, the hip joint is a ball and socket joint which provides universal motion.

Various diseases, such as osteoarthritis, attack the hip joint, and when this occurs, it may be necessary to utilize an appropriate hip joint prosthesis to replace the femoral head and the acetabulum. This may also be necessary in other circumstances, such as in the case of certain hip joint fractures.

Deterioration of the acetabulum requires that an acetabular cup be mounted in the acetabulum to provide a socket for slidably receiving the prosthetic femoral head. Typically the acetabular cup is cemented in the acetabulum.

It is very important that the acetabular cup be securely mounted within the acetabulum. If it is not, surgery may be required to remedy the problem.

It is known to provide the outer surface of an acetabular cup with grooves which interlock with the cement to more securely affix the acetabular cup within the acetabulum. Although the grooves are of assistance, it is desirable to provide even better attachment between the acetabular cup and the cement.

Following hip surgery, it is desirable to determine the orientation of the acetabular cup and to monitor cup wear. Because acetabular cups are typically constructed of a plastic material, they cannot be seen on an X ray. Accordingly, some prior art cups include an annular or nearly annular marker wire of radiopaque material carried by an equitorial zone of the cup. Although such a marker wire is of use in determining cup orientation, it may not provide all of the orientation information that is desired, and such a marker does not provide wear information at the polar region of the cup.

SUMMARY OF THE INVENTION

This invention provides an acetabular cup which can be cemented more securely into the acetabulum than was possible heretofore. Accordingly, the likelihood of the acetabular cup becoming loose is reduced. In addition, the orientation of the acetabular cup of this invention can be accurately determined following completion of hip surgery, and wear on the polar region of the cup as a result of contact with the femoral component of the prosthesis can be monitored.

The features of this invention are applicable to an acetabular cup which is of approximately hemispherical configuration and has an outer surface with a generally part-spherical contour. The acetabular cup also has an inner concave bearing surface of part-spherical configuration adapted to receive the femoral head. The outer surface of the acetabular cup preferably has grooves defining segments on the outer surface of the cup. In use of the acetabular cup, the cement interlocks with the surfaces defining these grooves to provide an interlock between the cement and the cup.

To more securely interlock the cement with the acetabular cup, one or more of the grooves is undercut to define a flange. This enables some of the cement to extrude behind the flange to increase the strength of the interlock and to tend to resist removal of the acetabular cup from the acetabulum.

The acetabular cup may have both latitude and longitude grooves. Although either or both of the latitude and longitude grooves may be undercut to define a flange, preferably at least one of the latitude grooves is undercut. Preferably the latitude groove which is most remote from a polar region of the acetabular cup is undercut. By undercutting this latitude groove, an overhanging flange of maximum surface area and length is provided. Preferably the groove has opposed edges, and each of the edges is undercut to define opposed overhanging flanges. Because of the presence of one or more overhanging flanges, the groove is wider at the base than the mouth.

The outer surface of the acetabular cup has pods or spacer lugs and a continuous flange receivable in the acetabulum which are engageable with the surface of the acetabulum to assist in positioning the cup within the acetabulum. The flange also increases cement intrusion pressure during cup insertion. The lugs and flange assure that substantially equal thicknesses of cement will exist along the outer surface of the acetabular cup and help assure a more uniform load transfer to the bone while minimizing the likelihood of eccentric placement of the cup.

It is desirable to have the wall thickness of the cup be substantially uniform, except, of course, for the presence of the grooves and lugs. This can be advantageously accomplished by making the bearing surface and the outer surface substantially concentric. If these two surfaces were non-concentric, the wall thickness of the cup would vary throughout the cup, and this would increase the likelihood that differential stress distribution would loosen the cup from the acetabulum.

To provide additional information with respect to the orientation and position of the acetabular cup, the cup has a radiopaque marker in the polar region of the cup. The marker can be seen on an X ray and, therefore, it indicates the position of the polar region of the acetabular cup. In addition, the spacing between the marker and the head of the prosthetic femoral component can also be seen on an X ray so that wear of the acetabular cup can be monitored.

In order to best accomplish these purposes, the acetabular cup has a spacer lug in the polar region, and the radiopaque marker is in the form of a short pin embedded in that spacer lug. The short pin minimizes the cost of the marker. The spacer lug provides a convenient structure into which the marker can be embedded and positively prevents the marker from becoming dislodged. Preferably, the marker does not project substantially beyond the spacer lug.

The invention, together with additional features and advantages thereof, may best be understood by reference to the following description taken in connection with the accompanying illustrative drawing.

BRIEF DESCRIPTION OF THE DRAWING

FIG. 3 is an exploded perspective view of the protrusio cup.

FIG. 4 is a sectional view taken generally along line 4—4 of FIG. 3.

FIGS. 5 and 6 are sectional views taken generally along lines 5—5 and 6—6, respectively, of FIG. 4.

FIG. 7 is an exploded isometric view of an acetabular cup constructed in accordance with the teachings of this invention.

FIG. 8 is a top plan view of the acetabular cup.

FIGS. 9 and 10 are sectional views taken generally along lines 9—9 and 10—10 of FIG. 2, respectively.

FIGS. 11, 12 and 13 are enlarged fragmentary sectional views showing the regions of the cup adjacent the polar lug, the lower latitude groove and the upper latitude groove, respectively.

FIG. 14 is a sectional view illustrating the acetabular cup implanted in the acetabulum.

DESCRIPTION OF THE PREFERRED EMBODIMENTS

Figure 1:
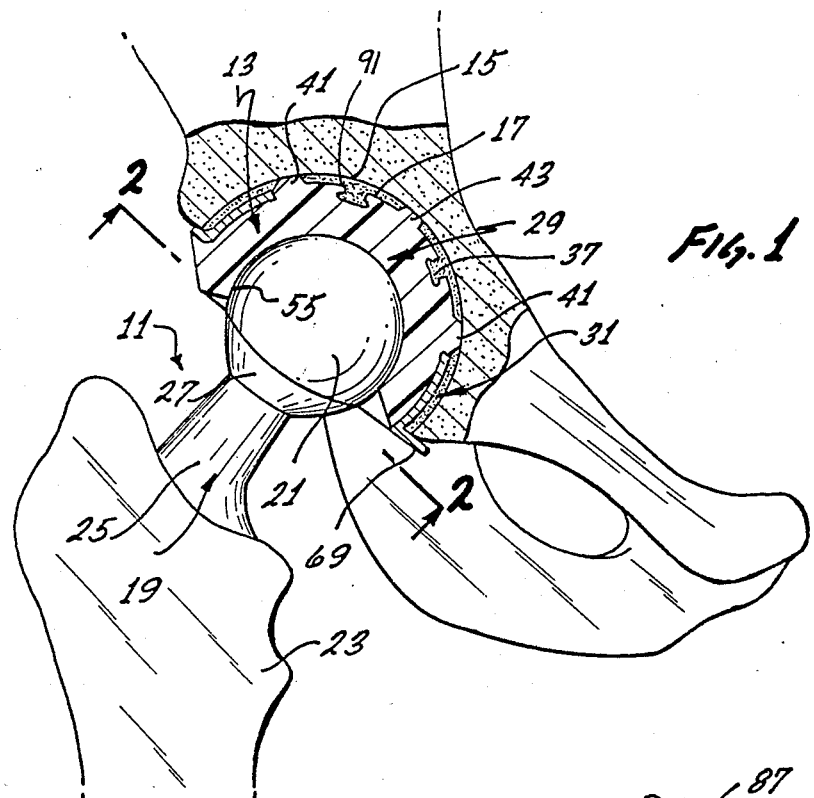
FIG. 1 is a front elevational view partially in section showing the invention embodied in a protrusio cup which is used in a hip joint prosthesis for the right hip.

FIG. 1 shows a hip joint prosthesis 11 which includes a protrusio cup 13 retained in the acetabulum 15 by bone cement 17 and a femoral component 19 having a femoral head 21 slidably received within the protrusio cup 13. The protrusio cup 13 can be used with femoral components of various different constructions. The femoral component 19, which is shown by way of example, also comprises a stem (not shown) which is inserted into the femur 23 and a neck 25 for joining the femoral head 21 to the stem. The femoral head 21 is essentially spherical, except for one or more conical portions 27 adjacent the neck 25.

The protrusio cup 13 comprises an acetabular cup 29 and a protrusio shell 31. The acetabular cup 29 is preferably molded of a suitable biocompatible plastic material, such as polyethylene. Although the acetabular cup 29 is of approximately hemispherical configuration, it is, in this preferred embodiment, not geometrically hemispherical in that, as set forth more particularly hereinbelow, it extends for more than 180 degrees on one side and its outer surface is irregular. Although the acetabular cup 29 of this invention is particularly adapted for use with the protrusio shell 31, it can be used without a protrusio shell or with protrusio shells other than the shell 31.

The acetabular cup 29 has an outer surface 33 with a generally part-spherical contour and an inner concave bearing surface 35 of part-spherical configuration adapted to receive the femoral head 21. The surfaces 33 and 35 are concentric. To provide a better interlock with the cement 17, the outer surface 33 is preferably of irregular configuration and, for this purpose, has an annular latitude groove 37 (FIG. 3) and a plurality of longitude grooves 39 which intersect the latitude groove to define segments 40 (FIG. 3). A plurality of pods or spacer lugs 41 is arranged in a ring with each of the lugs 41 being on a segment 40 intermediate an adjacent pair of longitude grooves 39. In addition, a spacer lug 43 is provided on a segment 40 coaxially with the annular latitude groove 37.

As shown in FIG. 1, these lugs 41 and 43 engage the wall of the acetabulum 15 to provide an even thickness of the cement 17. In addition, the spacer lugs transfer force to the bone and aid in properly positioning of the protrusio cup 13 within the acetabulum 15.

The acetabular cup 29 defines a cavity 44 which opens at a mouth. As best shown in FIGS. 1, 2, 4 and 6, the bearing surface 35 terminates in a free edge which lies in planes 45 and 47 which intersect along a line 49 to define an obtuse angle which opens outwardly of the cavity 44. Although different angles can be used, in the embodiment illustrated, the obtuse angle is 165 degrees. As shown in FIG. 4, the line 49 is spaced from the center 51 of the outer surface 33 and the bearing surface 35. An extension of the plane 45 along dashed line 53 extends through the center 51 and divides the bearing surface 35 into a hemispherical 180 degree portion on one side of the plane 45 and a part-spherical bearing surface extension 55 on the other side of the plane 45 and between dashed line 53 and the second plane 47. In the embodiment illustrated, the angle defined by the plane 47 and the dashed line 53 is 15 degrees and this is the preferred angle.

When the cavity 44 receives the femoral head 21, the plane 45 lies generally along the equator of the femoral head. However, the plane 47 lies below the equator. In other words, the bearing surface extension 55 forms a sector of a sphere which extends beyond the hemisphere but only on one side of the line 49. For this reason, the ability of the acetabular cup 29 to grip the femoral head 21 is much less than if the entire edge of the cavity 44 extended beyond the hemisphere of the femoral head.

The outer surface 33 terminates in a free edge which lies in planes 45a and 47a which intersect at a point 49a to define an angle which is only slightly less than 180 degrees and which opens outwardly. The planes 45 and 45a are parallel. The lines 49 and 49a define the cutting plane 5—5 which is perpendicular to the plane 45.

The acetabular cup 29 has a sloping surface 57 which leads from the bearing surface 39 radially outwardly to allow the maximum potential range of motion. A portion of the sloping surface 57 lies within the plane 47.

Although the protrusio shell 31 can be mounted in different ways on the acetabular cup 29, in the embodiment illustrated, the cup has an annular groove 59 for receiving the protrusio shell. The groove 59 is defined by a shoulder 61 along one circumferential edge and a circumferentially extending flange 63 along the other circumferential edge. The shoulder 61 is interrupted by the longitude grooves 39 (FIG. 3). The flange is discontinuous and defines a radial gap 64 (FIG. 3). As shown in FIG. 4, an outer sloping surface 65 extends from the flange 63 to the sloping surface 57 in the region of the bearing surface extension 55. Thus, the bearing surface extension 55 is formed on an extension of the acetabular cup 29 which projects beyond the groove 59.

The protrusio shell 31 is preferably integrally constructed of a suitable biocompatible metal. The protrusio shell 31 comprises an annular segment 67 and three flanges 69, 71 and 73 projecting radially outwardly from the wide end of the annular segment. The flanges 69, 71 and 73 are spaced circumferentially by a radially short ledge 74 which extends continuously between the adjacent flanges. The centers of the flanges 69 and 71 are preferably equally spaced, and the radial dimension of the flange 69 is less than the radial dimension of the other two flanges. The radial dimensions of the flanges 71 and 73 are preferably equal. The annular segment 67 has a part spherical outer surface 75 and a concentric, part spherical inner surface 77. The protrusio shell 31 is open at both ends.

The protrusio shell 31 has an edge 79 at one end and edges 81 and 83 at the other end. The edge 81 has two notches 84 (FIG. 5). The edge 81 (except for the notches 84) and the edge 83 lie in planes which intersect at the line 49a to define an obtuse angle which opens inwardly toward the cavity 44. The flange 69 lies in the same plane with the unnotched portion of the edge 81, and the flanges 71 and 73 lie in the same plane with the edge 83. The edge 79 is not parallel to either of the edges 81 or 83 in the embodiment illustrated.

Figure 2:
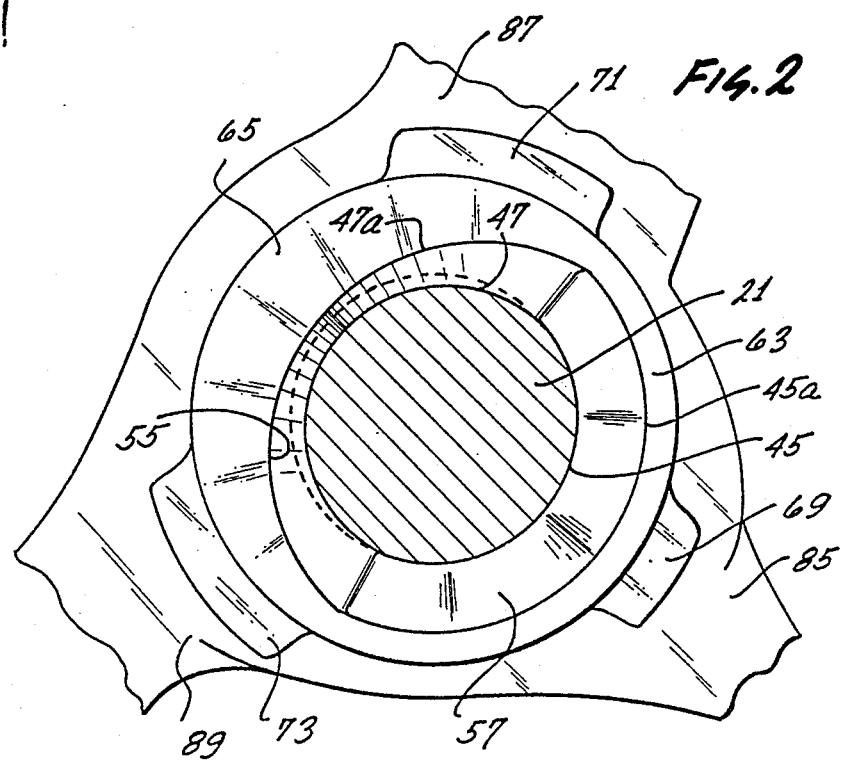
FIG. 2 is an enlarged fragmentary sectional view taken generally along line 2—2 of FIG. 1.

The protrusio shell 31 is mounted in the groove 59 of the acetabular cup during manufacture of the protrusio cup 13. The shell 31 is mounted snugly within the groove 59 with the ledge 74 and the flanges 71 and 73 resting on the flange 63 of the acetabular cup. The flange 69 is snugly received within the gap 64. As shown in FIG. 2, the flanges 71 and 73 project radially outwardly from the opposite ends of the bearing surface extension 55, and the flanges 71 and 73 are spaced apart circumferentially to provide a gap over the central region of the bearing extension surface 55.

When mounted in this manner, the plane 45a and the plane of the unnotched portion of the edge 81 are preferably substantially the same. The portion of the cup 29 which defines the bearing surface extension 55 is essentially not surrounded by the protrusio shell 31, and the bearing surface extension projects through the plane of the edge 83 of the protrusio shell. The annular edge 79 is skewed on the cup 29 in that a plane passing through the center 51 perpendicular to the plane of the edge 79 would not bisect the plane of the edge 79.

In use, the protrusio cup 13 can be implanted as a unit into the acetabulum 15, and this simplifies the operative procedure and eliminates the necessity of having to position the acetabular cup and the protrusio shell relative to each other. As shown in FIG. 1 and 2, the bearing surface extension 55 lies primarily in the superior-posterior region and has its maximum extension posteriorly of the most superior position. For example, the maximum extension may be displaced 30 degrees to 45 degrees from the most superior position. When so positioned, portions of the bearing surface extension 55 are also in the superior-anterior and inferior-posterior regions as shown in FIG. 2. The flanges 69, 71 and 73 are spaced circumferentially so that they engage the pubis 85, ischium 87 and iliac, respectively, to transfer loads to the bony regions they engage. The absence of any flange between the ilium and ischium avoids grinding of the femoral head against such flange in case of dislocation.

As shown in FIG. 1, the bone cement 17 interlocks with the surfaces defining the latitude groove 37 and the longitude groves 39 and with the lugs 41 and 43 to provide an interlock between the bone cement 17 and the acetabular cup 29. To increase the strength of this interlock, the latitude groove 37 is undercut to define opposed overhanging flanges 91 (FIGS. 1, 4 and 5). Consequently, the latitude groove 37 is wider at its base, i.e., radially inwardly of the flanges 91, than it is at its mouth, i.e., the region of the latitude groove 37 at the outer surface of the flanges 91. As shown in FIG. 1, some of the cement 17 can extrude beneath or behind the flanges 91 to increase the strength of the interlock and to tend to resist removal of the acetabular cup 29 from the acetabulum 15.

FIGS. 7-14 show an acetabular cup 29a embodying the features of this invention. Portions of the acetabular cup 29a corresponding to portions of the acetabular cup 29 are designated by corresponding reference numerals followed by the letter "a."

The acetabular cup 29a is preferably molded of a suitable biocompatible plastic material, such as polyethylene. The acetabular cup 29a has an equator 100 (FIGS. 9 and 10), and the portion of the cup above the equator is essentially a hemisphere. Although the acetabular cup 29a is of approximately hemispherical configuration, it is, in this embodiment, not geometrically hemispherical in that it extends for slightly more than 180 degrees, i.e., it extends below the equator 100, and its outer surface is irregular.

The acetabular cup 29 has an outer surface 33a with a generally part-spherical contour and an inner concave bearing surface 35a of part-spherical configuration adapted to receive a femoral head, such as the femoral head 21a (FIG. 14). The surfaces 33a and 35a are concentric and have a common center 102. To provide an interlock with the cement 17a (FIG. 14), the outer surface 33a is of irregular configuration and for this purpose has annular latitude grooves 37a and 101 (FIGS. 7 and 10) and a plurality of longitude grooves 39a which intersect the latitude grooves 37a and 101 to define segments 40a and a polar segment 103. More specifically, each of the longitude grooves 39a extends from the latitude groove 37a continuously through the latitude groove 101 to interrupt the latter and terminates in an end portion 105 in an annular ridge 107 just below, or on the equator side of, the latitude groove 101. The longitude grooves 39a are equally spaced in the equatorial direction so that the segments 40a are of equal size.

The polar segment 103 is circular in plan as shown in FIG. 8 and is coaxial with a polar axis 108 (FIGS. 9 and 10) of the acetabular cup 29a. The polar axis 108 is equally spaced from all points on the equator of the acetabular cup, and the center 102 is at the intersection of the equator 100 and the polar axis 108.

A plurality of pods or spacer lugs 41a is arranged in a ring, with each of the lugs 41a being on a segment 40a intermediate an adjacent pair of the longitude grooves 39a. Each of the lugs 41a is centered on its associated segment 41a in the equatorial direction and located slightly closer to the latitude groove 101 than to the latitude groove 37a. Of course, this positioning of the lugs 41a is not essential. In addition, a spacer lug 43a is provided on the polar segment 103 coaxially with the polar segment. The lugs 41a and 43a perform the same function as do the lugs 41 and 43 of the embodiment of FIGS. 1-6, and they have outer ends or outer surfaces 110 which are equally spaced from the center 102.

The latitude groove 37a differs from the latitude groove 37 in that it has parallel side walls 109 (FIG. 13) and no flanges corresponding to the flanges 91. Thus, the latitude groove 37a has a base 111 and a mouth 113 of equal width.

The latitude groove 101 has undercuts 115 defining opposed overhanging flanges 91a. Although various constructions can be employed, the latitude groove 101 has sloping side walls 117 which slope toward each other as they extend from a base 119 toward a mouth 121. Thus, the groove 101 is wider at the base 119 than at the mouth 121.

The bearing surface 35a terminates at the equator 100 where it meets a frusto-conical surface 123 (FIGS. 9 and 10) which extends radially outwardly away from the equator 100 to an annular, flat end face 125. The acetabular cup 29a has a continuous, 360-degree, circumferential flange 127 which extends completely around the exterior of the cup at the mouth of the cavity in the cup, and the end face 125 forms one boundary of the flange. The flange 127 has an outer peripheral surface 128 of generally circular configuration which is spaced from the center 102 by a distance equal to, or approximately equal to, the distance between the center 102 and the outer ends 110 of the lugs 41a and 43a. Stated differently, the flange 127 and the lugs 41a and 43a project equal distances beyond the part-spherical outer surface 33a, and such distance may be, for example, about 2.5 mm. This enables the flange 127 to be received within the acetabulum 15a and cooperate with the lugs 41a and 43a to space the cup from the surface of the acetabulum. The cup 29a has an annular marker groove 129 in the outer surface 33a on the side of the flange 127 opposite the end face 125. A radiopaque marker in the form of a split ring wire 131 is retained within the marker groove 129.

A radiopaque marker in the form of a short pin 133 of radiopaque material is embedded in the polar lug 43a as best shown in FIG. 11. In this embodiment, the pin 133 does not project beyond the exterior surface of the polar lug 43a.

In use, the acetabular cup can be cemented into the acetabulum 15a using the bone cement 17a (FIG. 14) and conventional techniques. The continuous flange 127 is received within the acetabulum, with the peripheral surface 128 slightly spaced from the wall of the acetabulum to assist in concentric placement of the acetabular cup 29a. Because the flange 127 is continuous, it increases cement intrusion pressure during cup insertion. The lugs 41a and 43a and the flange 127 insure a cement mantle of uniform thickness, insure more uniform load transfer, and facilitate concentric placement of the cup in the acetabulum 15a. A cement mantle of uniform thickness reduces the tendency of the cement to fracture. The frusto-conical surface 123 provides for an increased range of motion and prevents point contact with the neck 25a of the femoral component 19a. The acetabular cup 29a has its corners rounded to prevent stress risers.

The cement 17a is forced or extruded into the grooves 37a, 39a and 101 and beneath or behind the overhanging flanges 91a. Consequently, the flanges 91a interlock with the bone cement 17a to securely retain the cup 29a in the acetabulum 15a. Because the flanges 91a are in the latitude groove 101, which is near the equator 100, a long and large surface area is provided by the side walls 117 to provide for greater interlocking strength. The lugs 41a and 43a cooperate with the undercut groove 101 to increase the resistance of the cup to torsional forces. Consequently, there is substantial resistance to forces tending to move the acetabular cup from the acetabulum.

The ring 131 and the pin 133 cooperate to provide for accurate assessment of placement of the cup 29a in the acetabulum 15a in that they can readily be seen on an X ray. The pin 133 is of particular advantage in that its position relative to the femoral head 21 can readily be seen in an X ray so that wear at the polar region of the cup 29a can be easily assessed. The preferred location of the pin 133 in the radial direction is at the base of the polar lug 43a so that the radial inner surface of the pin is substantially flush with the adjacent regions of the polar segment 103 as shown in FIG. 11. The ring 131 is useful in assessing the anteversion and abduction angles of the cup 29a.

Although an exemplary embodiment of the invention has been shown and described, many changes, modifications and substitutions may be made by one having ordinary skill in the art without necessarily departing from the spirit and scope of this invention.

I claim:

1. An acetabular cup of approximately hemispherical configuration adapted for implantation in the acetabulum, said acetabular cup having an outer surface with a generally part-spherical contour and an inner concave being surface adapted to receive a femoral head said outer surface having a plurality of grooves defining segments on the outer surface, said grooves being adapted to receive and interlock with a cement for affixing the acetabular cup within the acetabulum, at least one of said grooves having at least one undercut which defines an overhanging flange whereby the cement can be received in said one groove behind the flange to interlock with the flange and tend to resist loosening of the acetabular cup from the acetabulum, said grooves including a plurality of latitude grooves and said one groove is the latitude groove which is most remote from a polar region on the acetabular cup, each of at least some of said segments having at least one spacer lug on the outer surface thereof to assist in positioning the acetabular cup in the acetabulum.

2. An acetabular cup as defined in claim 1 wherein at least one of said segments which has at least one of said spacer lugs thereon is in a polar region of said acetabular cup and said acetabular cup includes a short pin of radiopaque material embedded in said spacer lug of said one segment.

3. An acetabular cup as defined in claim 1 including a continuous flange extending around the base of the acetabular cup for facilitating concentric placement of the acetabular cup and increasing the cement intrusion pressure during cup insertion, said outer surface has a center and the distance from said center to the outer surface of said one spacer lug is approximately equal to the distance from said center to the outer surface of said flange.

4. An acetabular cup as defined in claim 1 wherein said one groove has opposed edges and each of said edges is undercut to define opposed overhanging flanges.

5. An acetabular cup as defined in claim 1 wherein said one groove is wider at its base than at its mouth.

6. An acetabular cup as defined in claim 1 including a continuous flange extending around the base of the acetabular cup for facilitating concentric placement of the acetabular cup and increasing the cement intrusion pressure during cup insertion.

7. An acetabular cup of approximately hemispherical configuration adapted for implantation in the acetabulum, said acetabular cup having an outer surface with a generally part-spherical contour and an inner concave bearing surface adapted to receive a femoral head, said acetabular cup including a plurality of spacer lugs on the outer surface to assist in positioning the acetabular cup in the acetabulum, at least one of said spacer lugs being in the polar region of said outer surface of said acetabular cup, and a radiopaque marker in said one spacer lug, said radiopaque marker including a short pin of radiopaque material embedded in said one spacer lug, said radiopaque marker not projecting substantially beyond said one spacer lug.

8. An acetabular cup as defined in claim 7 wherein said outer surface has a plurality of grooves defining segments on the outer surface and at least some of said spacer lugs are on said segments and said grooves are adapted to receive and interlock with a cement for affixing the acetabular cup in the acetabulum.

9. An acetabular cup as defined in claim 8 wherein at least one of said segments is in a polar region of the acetabular cup and said one spacer lug is on said one segment and said acetabular cup includes a continuous flange extending around the base of the acetabular cup for facilitating concentric placement of the acetabular cup and increasing the cement intrusion pressure during cup insertion, a marker groove in the outer surface adjacent the flange and extending in the latitude direction and a radiopaque marker received in said marker groove.

10. An acetabular cup adapted to be received in the acetabulum and being of approximately hemispherical configuration, said acetabular cup having an outer surface with a generally part-spherical contour, said acetabular cup having an inner concave bearing surface of part-spherical configuration defining a cavity which is adapted to receive a femoral head, said outer surface having a plurality of grooves defining segments on the outer surface, each of at least some of said segments having at least one spacer lug on the outer surface thereof to assist in positioning the acetabular cup in the acetabulum, each of said spacer lugs having an outer end, a continuous flange extending completely around the base of the acetabular cup for increasing the cement intrusion pressure during cup insertion, said flange having an outer peripheral surface of generally circular configuration, said outer surface of generally part-spherical contour having a center, the distance from said center to the outer ends of said spacer lugs being approximately equal to the distance from said center to said outer peripheral surface of said flange whereby the flange can be received within the acetabulum and cooperate with the lugs to facilitate concentric placement of the cup in the acetabulum.

11. An acetabular cup as defined in claim 1 including cement at least in said one groove for affixing the acetabular cup in the acetabulum.

12. An acetabular cup of approximately hemispherical configuration adapted for implantation in the acetabulum, said acetabular cup having an outer surface with a generally part-spherical contour and an inner concave bearing surface adapted to receive a femoral head, said outer surface having a plurality of grooves defining segments on the outer surface, said grooves being adapted to receive and interlock with a cement for affixing the acetabular cup within the acetabulum, at least one of said grooves having at least one undercut which defines an overhanging flange whereby the cement can be received in said one groove behind the flange to interlock with the flange and tend to resist loosening of the acetabular cup from the acetabulum, said grooves including a plurality of latitude grooves and said one groove is the latitude groove which is most remote from a polar region of the acetabular cup, said cup being constructed of plastic material, said outer and inner surfaces being substantially concentric, said one groove having opposed edges and each of said edges being undercut to define opposed overhanging flanges and each of at least some of said segments having at least one spacer lug on the outer surface thereof to assist in positioning the acetabular cup in the acetabulum.

13. An acetabular cup as defined in claim 12 wherein at least one of said segments which has at least one of said spacer lugs thereon is in the polar region of the acetabular cup and said acetabular cup includes a first radiopaque marker in said spacer lug of said one segment.

14. An acetabular cup as defined in claim 13 including a continuous flange extending around the base of the acetabular cup for facilitating concentric placement of the acetabular cup and increasing the cement intrusion pressure during cup insertion, a marker groove in the outer surface adjacent the flange and extending in the latitude direction and a second radiopaque marker received in said marker groove.

* * * * *

UNITED STATES PATENT AND TRADEMARK OFFICE
CERTIFICATE OF CORRECTION

PATENT NO. : 4,883,490

DATED : Nov. 28, 1989

INVENTOR(S) : Indong Oh

It is certified that error appears in the above—identified patent and that said Letters Patent is hereby corrected as shown below:

Column 8, line 5 change "being" to -- bearing --.

Signed and Sealed this

Twenty-sixth Day of March, 1991

Attest:

HARRY F. MANBECK, JR.

*Attesting Officer*

*Commissioner of Patents and Trademarks*